United States Patent [19]
Halloran

[11] Patent Number: 6,153,569
[45] Date of Patent: Nov. 28, 2000

[54] OPTICALLY CLEAR SHAMPOO COMPOSITIONS CONTAINING AMINOFUNCTIONAL SILICONE MICROEMULSIONS

[75] Inventor: Daniel Joseph Halloran, Midland, Mich.

[73] Assignee: Dow Corning Corporation, Midland, Mich.

[21] Appl. No.: 09/122,389

[22] Filed: Jul. 24, 1998

Related U.S. Application Data

[63] Continuation-in-part of application No. 07/705,455, May 24, 1991, abandoned.

[51] Int. Cl.[7] .................................. C11D 1/38; C11D 1/02
[52] U.S. Cl. ........................ 510/119; 510/121; 510/122; 510/123; 510/124; 510/466; 510/131; 510/151; 510/471; 510/473; 424/70.12; 424/70.13
[58] Field of Search ..................... 510/121, 122, 510/123, 124, 466, 135, 137, 151, 471, 473, 6; 424/70.12, 70.13

[56] References Cited

U.S. PATENT DOCUMENTS

| | | | |
|---|---|---|---|
| 2,781,354 | 2/1957 | Mannheimer | 546/352.1 |
| 4,275,055 | 6/1981 | Nachtigal | 424/70.19 |
| 4,374,125 | 2/1983 | Newell | 424/20 |
| 4,387,090 | 6/1983 | Bolich | 424/70.12 |
| 4,559,227 | 12/1985 | Chandra | 510/122 |
| 4,563,347 | 1/1986 | Starch | 424/70.12 |
| 4,586,518 | 5/1986 | Cornwall | 424/70.12 |
| 4,601,902 | 7/1986 | Fridd | 424/70.122 |
| 4,618,689 | 10/1986 | Traver | 424/70.12 |
| 4,620,878 | 11/1986 | Gee | 516/55 |
| 4,733,677 | 3/1988 | Gee | 424/70.12 |
| 4,749,732 | 6/1988 | Kohl et al. | 524/413 |
| 4,788,006 | 11/1988 | Bolich | 510/121 |
| 4,933,176 | 6/1990 | Reeth | 424/70.121 |
| 4,997,641 | 3/1991 | Harnett et al. | 51/295 |
| 5,049,377 | 9/1991 | Lamb et al. | 424/70.121 |
| 5,063,044 | 11/1991 | Kohl | 424/217 |
| 5,077,040 | 12/1991 | Bergmann et al. | 424/70.122 |
| 5,087,443 | 2/1992 | Chizat | 424/70.121 |
| 5,108,738 | 4/1992 | Halloran et al. | 424/70.14 |
| 5,126,126 | 6/1992 | Varpath | 424/70.12 |
| 5,132,443 | 7/1992 | Traver et al. | 556/425 |
| 5,145,607 | 9/1992 | Rich | 252/547 |
| 5,152,914 | 10/1992 | Forster et al. | 252/174 |
| 5,160,449 | 11/1992 | Halloran | 510/418 |
| 5,240,698 | 8/1993 | Tracer et al. | 424/71 |
| 5,326,483 | 7/1994 | Halloran et al. | 252/124.15 |
| 5,578,298 | 11/1996 | Berthiaure et al. | 424/70.122 |
| 5,679,331 | 10/1997 | Hase | 424/70.19 |
| 5,747,436 | 5/1998 | Patel et al. | 510/124 |
| 5,776,871 | 7/1998 | Cothran et al. | 510/122 |
| 5,856,544 | 1/1999 | Czech et al. | 556/425 |

OTHER PUBLICATIONS

Dow Corning Corp. Corporate Test Method CTM0851. "Turbidity of Liquids by Light Scattering." Jun. 17,.
Dow Corning Corp. Corporate Test Method CTM 0004. "Vicosity–Glass Capillary Viscometer." Jul. 29, 1970.
Schwartz et al. "Surface Active Agents–Their Chemistry & Technology." 1949, Chapters 7 & 8.
"McCutcheon's Emulsifiers & Detergents." North American Edition, 1989, pp. 257 & 258.
Schwartz et al. "Surface Active Agents & Detergents." 1977, vol. II, Chapter 4.

*Primary Examiner*—Kery Fries
*Attorney, Agent, or Firm*—Timothy J. Troy

[57] ABSTRACT

This invention relates to the use of aminofunctional silicone microemulsions to make optically clear compositions. More particularly this invention is directed to optically clear shampoo compositions comprising (A) an aminofunctional silicone microemulsion having an average particle size of less than 0.06 microns, (B) at least one anionic detersive surfactant, (C) at least one foam boosting agent, (D) at least one pH adjusting agent, (E) at least one thickening agent, and (F) water. The optically clear silicone compositions of this invention are useful in the hair care industry, especially as shampoos.

22 Claims, No Drawings

OPTICALLY CLEAR SHAMPOO COMPOSITIONS CONTAINING AMINOFUNCTIONAL SILICONE MICROEMULSIONS

CROSS REFERENCE TO RELATED APPLICATIONS

This is a continuation-in-part of Ser. No. 07/705,455, filed on May 24, 1991, abandoned.

FIELD OF THE INVENTION

This invention relates to the use of aminofunctional silicone microemulsions to make optically clear shampoo compositions. More particularly this invention is directed to an optically clear shampoo composition comprising an aminofunctional silicone microemulsion, at least one anionic detersive surfactant, at least one foam boosting agent, at least one pH adjusting agent, at least one thickening agent, and water.

BACKGROUND OF THE INVENTION

It is desirable to provide compositions which have beneficial effects on wet and dry hair, for example which improve handle, softness, silkiness, and ease of combing the hair. Such beneficial effects may be obtained by incorporating certain types of silicones into hair care compositions. The preferred silicones include alkyl- or aryl-functional polydiorganosiloxanes. However, such compounds are not easily incorporated and result in opaque or at best translucent hair care products. It is aesthetically desirable to provide optically clear hair care compositions.

Silicones in hair care compositions have been disclosed in a number of different publications. For example, in U.S. Pat. No. 4,788,006 is disclosed shampoo compositions which comprise a synthetic, anionic surfactant, a dispersed, insoluble, non-volatile silicone, a xanthan gum suspending agent and water.

Hair treating compositions containing aminofunctional polysiloxanes have also been described. For example, in U.S. Pat. No. 4,563,347 it is disclosed that an aqueous emulsion of aminoalkyl substituted polydimethylsiloxane is useful to condition hair because it facilitates combing and imparts a smooth feel to hair. The aminoalkyl substituents are credited with providing the copolymers with cationic sites that make the polymer more substantive to hair than nonsubstituted polydimethylsiloxane. The '347 patent further teaches the use of aminofunctional polydiorganosiloxane solutions and emulsions as conditioners. Other hair treating compositions containing amino functional polysiloxanes are described in U.S. Pat. Nos. 4,586,518, 4,601,902, and 4,618,689, however these references do not describe the use of microemulsions in these compositions.

Aminofunctional microemulsions have also been described in the art. For example, in U.S. Pat. No. 4,749,732 is disclosed the use polydiorganosiloxanes containing aminoalkyl groups modified by alkoxycarbonylalkyl substituents in hair care compositions. The '732 patent also teaches that the modified aminoalkyl silicones exhibit improved deposition on hair and can be formulated into shampoos or conditioners. The '732 patent states that microemulsions of modified aminoalkyl substituted polydiorganosiloxane can be prepared by the method described in U.S. Pat. No. 4,620,878 which describes generally the preparation of emulsions of silicones containing polar substituents. The '732 patent does not disclose how to prepare these modified aminoalkyl substituted polydiorganosiloxane microemulsions. Further the '732 patent does not disclose an unmodified or unsubstituted amino functional microemulsion as an ingredient in an optically clear silicone formulation. In addition, these modified amino substituted microemulsions utilize acrylic monomers which give rise to serious odor problems making the materials unsuitable for cosmetic use.

The '878 patent teaches a method of preparing clear microemulsions of aminofunctional polyorganosiloxanes. It is further disclosed in Example 24 of the '878 patent that transparent microemulsions of aminofunctional siloxanes can be mixed with a shampoo base of sodium laurel ether sulfate and water to produce a stable, clear composition. However, the '878 patent does not teach an aminofunctional microemulsion as an ingredient present in an optically clear shampoo composition. Example II and Comparative Example I of this specification clearly illustrate the unexpected advantages of this invention over the composition described in Example 24 of the '878 patent.

In U.S. Pat. No. 4,559,227 a conditioning shampoo composition is taught containing a nonionic surfactant of the alkanolamide or amine oxide type, an aminofunctional polydiorganosiloxane as a hair conditioning component, a detersive surfactant of the anionic or amphoteric type, and water, the shampoo composition being in the form of an aqueous solution. The '227 patent further discloses a method of preparing the shampoo composition as a stable solution. This is in contrast to this invention which employs pre-made microemulsions as opposed to solutions as components to provide optically clear silicone compositions. The use of the premade microemulsion allows an easier to use shampoo to be formed without a complex premixing of the composition.

Polydiorganosiloxane microemulsions have also been described in the hair care art. For example, European Patent Publication No. 268,982 discloses cosmetic compositions containing microemulsions of dimethylpolysiloxanes produced by emulsion polymerization which provide long term storage stability. However, the formulations of the '982 application do not disclose a aminofunctional silicone microemulsion as an ingredient in an optically clear silicone composition that provides substantive conditioning.

In U.S. Pat. No. 5,063,044 is disclosed a hair conditioning composition being a mixture including water, a thickener, and an organosilicon compound. The organosilicone compound can take the form of a microemulsion and is selected from the group consisting of carboxy glycol ether and carboxy-glycol ester functional polysiloxanes, which are appreciably polar and soluble molecules. In contrast, this invention utilizes a non-polar insoluble aminofunctional polydiorganosiloxane microemulsion in combination with certain materials to unexpectedly provide true optical clarity to the silicone compositions of this invention along with robust, substantive conditioning when applied to hair.

This invention can therefore be distinguished from the references enumerated above in that this invention contains an aminofunctional silicone microemulsion in combination with certain materials to provide truly optically clear shampoo compositions that have beneficial effects greater than the hair care formulations known in the art, and in view of the fact that the cationic compounds of the prior art do not generally deposit well from shampoo compositions containing anionic detersive surfactants, it is surprising that the aminofunctional microemulsion is so effectively deposited from the shampoo compositions of this invention which can contain anionic detersive surfactants and at the same time retain clarity and stability. Therefore, since the shampoo compositions of this invention provide a unique and advantageous combination of superior foaming, and provide a clear and easy to use product with increased substantive conditioning properties, they are advantageous over the formulations of the art.

SUMMARY OF THE INVENTION

This invention is directed to an optically clear shampoo composition comprising an aminofunctional silicone microemulsion, at least one anionic detersive surfactant, at least one foam boosting agent, at least one pH adjusting agent, at least one thickening agent, and water.

The shampoo compositions of this invention are optically clear, easy to use, have outstanding conditioning, are easy to formulate, have excellent foaming, and are detergent compatible.

Microemulsions generally do not deposit well from shampoo compositions containing anionic detersive surfactants due to their excellent stability. It has been found that certain materials can aid in the deposition of the silicone microemulsions onto hair in shampoo compositions. The deposition of the microemulsion is enhanced due to the use of these certain materials. Surprisingly, the presence of anionic materials in the shampoo does not interfere with the clarity, stability, or the substantive properties of the silicone microemulsion.

DETAILED DESCRIPTION OF THE INVENTION

This invention also relates to an optically clear shampoo composition comprising (A) an aminofunctional silicone microemulsion having an average particle size of less than 0.06 microns, (B) at least one anionic detersive surfactant, (C) at least one foam boosting agent, (D) at least one pH adjusting agent, (E) at least one thickening agent, and (F) water.

For the purposes of this invention, the term "optically clear" is used to define a composition that is transparent (transmitting light without distortion) which means that the size of the particles in the composition are reduced to a size where they are not observable with optical (visual) means. According to this invention, "optically clear" is further defined by NTU's (Nephelometric Turbidity Units), which is the unit of measure for the turbidity or haze of a liquid. NTU's range from 0.04 to 1,000 or higher. A more detailed description of this test is found hereinbelow. The haze value of a relatively turbid solution is about 100 NTU's or higher, and mixtures with a slight haze give values of 20 to 50 NTU's. In contrast the compositions of this invention have an average haze value of 3 to 5 NTU's.

Component (A) is an aminofunctional silicone microemulsion. Microemulsions are mixtures of oil and water where the particle size of the resulting droplets is small enough so the resulting mixture is clear or translucent. Because of their relative clarity microemulsions are distinguishable from standard opaque emulsions in that certain microemulsions can be used to prepare clear cosmetics. The clarity of these compositions is advantageous in cosmetic applications such as in the hair care art. Microemulsions are also more temperature, dilution, and formulation stable than standard emulsions. Microemulsion droplet sizes are variously defined in the chemical art with an upper limit on the droplet size typically being placed somewhere between 0.10 and 0.15 micron to distinguish microemulsions from opaque standard emulsions. In general, microemulsions can also be defined by their appearance: microemulsions are transparent or translucent, and do not display the opalescence of standard emulsions. While microemulsions with average droplet sizes between 0.10 and 0.15 micron display the properties of microemulsions, microemulsions with average droplet sizes less than 0.06 micron are especially preferred for their even greater clarity and stability.

The aminofunctional microemulsions of this invention comprise (i) an aminofunctional polyorganosiloxane, (ii) at least one surfactant, and (iii) water.

Preferably the aminofunctional polyorganosiloxane of (A)(i) of this invention is a compound having its formula selected from the group consisting of

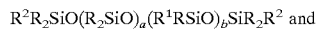
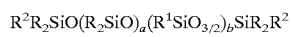

wherein R is a monovalent hydrocarbon radical, $R^1$ is an aminoalkyl group having its formula selected from the group consisting of —$R^3NH_2$ and —$R^3NHR^4NH_2$ wherein $R^3$ is a divalent hydrocarbon radical having at least 3 carbon atoms and $R^4$ is a divalent hydrocarbon radical having at least 2 carbon atoms, $R^2$ is selected from the group consisting of R, $R^1$, and —OH, a has a value of 0 to 2000, and b has a value of from greater than zero to 200.

The monovalent R radicals are exemplified by alkyl radicals such as the methyl, ethyl, propyl, butyl, amyl, and hexyl, alkenyl radicals such as the vinyl, allyl, and hexenyl, cycloalkyl radicals such as the cyclobutyl and cyclohexyl, aryl radicals such as the phenyl and naphthyl, aralkyl radicals such as the benzyl and 2-phenylethyl, alkaryl radicals such as the tolyl, and xylyl, halohydrocarbon radicals such as 3-chloropropyl, 4-bromobutyl, 3,3,3-trifluoropropyl, chlorocyclohexyl, bromophenyl, and chlorophenyl. It is preferred that R is a monovalent hydrocarbon radical having from 1 to 6 carbon atoms. Especially preferred R radicals are methyl, phenyl, and vinyl.

The group $R^3$ is preferably an alkylene radical having from 3 to 20 carbon atoms. Preferably $R^3$ is selected from the group consisting of propylene, —$CH_2CHCH_3$—, butylene, —$CH_2CH(CH_3)CH_2$—, pentamethylene, hexamethylene, 3-ethyl-hexamethylene, octamethylene, and decamethylene.

The group $R^4$ is preferably an alkylene radical having from 2 to 20 carbon atoms. Preferably $R^4$ is selected from the group consisting of ethylene, propylene, —$CH_2CHCH_3$—, butylene, —$CH_2CH(CH_3)CH_2$—, pentamethylene, hexamethylene, 3-ethyl-hexamethylene, octamethylene, and decamethylene.

It is highly preferred in this invention that $R^1$ is selected from the group consisting of —$CH_2CH_2CH_2NHCH_2CH_2NH_2$ and —$CH_2CH(CH_3)CH_2NHCH_2CH_2NH_2$.

Salts of these same aminofunctional radicals may also be used in this invention. Examples of such salts include alkyl carboxylate salts, aryl carboxylate salts, halide salts such as chlorides and bromides, and other neutralization products of the amines with organic acids.

Although the group $R^2$ can be selected from the group consisting of R, $R^1$, and —OH, it is preferred for purposes of this invention that $R^2$ is methyl or —OH.

It is preferred that the polyorganosiloxanes have from about 0.1 to 15 molar percent of the above described amino groups and most preferably from about 0.2 to 10 molar percent of the above described amino groups. In the above formulas, preferably a has a value of from 50 to 2000, and b has a value of 1 to 100. The aminofunctional polyorganosiloxanes useful in the this invention can be prepared by procedures well known in the art. Many of these polyorganosiloxanes are available commercially. Therefore their preparation will not be described here.

The microemulsion of component (A) also comprises (ii) at least one surfactant. The surfactant may be an anionic, cationic, nonionic, or amphoteric surfactant. The surfactants may be employed separately or in combinations of two or more.

Examples of suitable anionic surfactants include alkali metal sulforicinates, sulfonated glyceryl esters of fatty acids such as sulfonated monoglycerides of coconut oil acids, salts of sulfonated monovalent alcohol esters such as sodium oleylisethianate, amides of amino sulfonic acids such as the sodium salt of oleyl methyl tauride, sulfonated products of fatty acids nitriles such as palmitonitrile sulfonate, sulfonated aromatic hydrocarbons such as sodium alpha-naphthalene monosulfonate, condensation products of naphthalene sulfonic acids with formaldehyde, sodium octahydroanthracene sulfonate, alkali metal alkyl sulfates such as sodium lauryl sulfate, ammonium lauryl sulfate or triethanol amine lauryl sulfate, ether sulfates having alkyl groups of 8 or more carbon atoms such as sodium lauryl ether sulfate, ammonium lauryl ether sulfate, sodium alkyl aryl ether sulfates, and ammonium alkyl aryl ether sulfates, alkylarylsulfonates having 1 or more alkyl groups of 8 or more carbon atoms, alkylbenzenesulfonic acid alkali metal salts exemplified by hexylbenzenesulfonic acid sodium salt, octylbenzenesulfonic acid sodium salt, decylbenzenesulfonic acid sodium salt, dodecylbenzenesulfonic acid sodium salt, cetylbenzenesulfonic acid sodium salt, and myristylbenzenesulfonic acid sodium salt, sulfuric esters of polyoxyethylene alkyl ether including $CH_3(CH_2)_6CH_2O(C_2H_4O)_2SO_3H$, $CH_3(CH_2)_7CH_2O(C_2H_4O)_{3.5}SO_3H$, $CH_3(CH_2)_8CH_2O(C_2H_4O)_8SO_3H$, $CH_3(CH_2)_{19}CH_2O(C_2H_4O)_4SO_3H$, and $CH_3(CH_2)_{10}CH_2O(C_2H_4O)_6SO_3H$, sodium salts, potassium salts, and amine salts of alkylnaphthylsulfonic acid.

Examples of cationic surfactants include various fatty acid amines and amides and their derivatives, and the salts of the fatty acid amines and amides. Examples of aliphatic fatty acid amines include dodecylamine acetate, octadecylamine acetate, and acetates of the amines of tallow fatty acids, homologues of aromatic amines having fatty acids such as dodecylanalin, fatty amides derived from aliphatic diamines such as undecylimidazoline, fatty amides derived from aliphatic diamines such as undecylimidazoline, fatty amides derived from disubstituted amines such as oleylaminodiethylamine, derivatives of ethylene diamine, quaternary ammonium compounds and their salts which are exemplified by tallow trimethyl ammonium chloride, dioctadecyldimethyl ammonium chloride, didodecyldimethyl ammonium chloride, dihexadecyl ammonium chloride, alkyltrimethylammonium hydroxides such as octyltrimethylammonium hydroxide, dodecyltrimethylammonium hydroxide, or hexadecyltrimethylammonium hydroxide, dialkyldimethylammonium hydroxides such as octyldimethylammonium hydroxide, decyldimethylammonium hydroxide, didodecyldimethylammonium hydroxide, dioctadecyldimethylammonium hydroxide, tallow trimethylammonium hydroxide, coconut oil, trimethylammonium hydroxide, methylpolyoxyethylene cocoammonium chloride, and dipalmityl hydroxyethylammonium methosulfate, amide derivatives of amino alcohols such as betahydroxylethylstearylamide, and amine salts of long chain fatty acids.

Examples of nonionic surfactants include polyoxyethylene alkyl ethers, polyoxyethylene alkylphenol ethers, polyoxyethylene lauryl ethers, polyoxyethylene sorbitan monoleates, polyoxyethylene alkyl esters, polyoxyethylene sorbitan alkyl esters, polyethylene glycol, polypropylene glycol, diethylene glycol, ethoxylated trimethylnonanols, and polyoxyalkylene glycol modified polysiloxane surfactants.

Examples of the amphoteric surfactants that can be used include amino acid surfactants and betaine acid surfactants. Combinations of 2 or 3 types of nonionic surfactants, combinations of nonionic surfactants and anionic surfactants, and combinations of nonionic surfactants and cationic surfactants can also be employed as component (A)(ii).

Preferred surfactants as component (A)(ii) include trimethylnonyl polyethylene glycol ethers and polyethylene glycol ether alcohols containing linear alkyl groups having from 11 to 15 such as 2,6,8-trimethyl-4-nonyloxypolyethylene oxyethanol (6 EO) (sold as Tergitol®TMN-6 by OSi Specialties, A Witco Company, Endicott, N.Y.), 2,6,8-trimethyl-4-nonyloxypolyethylene oxyethanol (10 EO) (sold as Tergitol®TMN-10 by OSi Specialties, A Witco Company, Endicott, N.Y.), alkylene-oxypolyethylene oxyethanol ($C_{1-15}$ secondary alkyl, 9 EO) (sold as Tergitol®15-S-9 by OSi Specialties, A Witco Company, Endicott, N.Y.), alkylene-oxypolyethylene oxyethanol ($C_{11-15}$ secondary alkyl, 15 EO) (sold as Tergitol®15-S-15 by OSi Specialties, A Witco Company, Endicott, N.Y.), octylphenoxy polyethoxy ethanols having varying amounts of ethylene oxide units such as octylphenoxy polyethoxy ethanol (40 EO) (sold as Triton®405 by Rohm and Haas Company, Philadelphia, Pa.), nonionic ethoxylated tridecyl ethers available from Emery Industries, Mauldin, S.C. under the general tradename Trycol, alkali metal salts of dialkyl sulfosuccinates available from American Cyanamid Company, Wayne, N.J. under the general tradename Aerosol, polyethoxylated quaternary ammonium salts and ethylene oxide condensation products of the primary fatty amines, available from Armak Company, Chicago, Ill. under the tradenames Ethoquad, Ethomeen, or Arquad, and polyoxyalkylene glycol modified polysiloxanes. These preferred surfactants may also be obtained from other suppliers under different tradenames.

The surfactant (A)(ii) should be present in the microemulsion of component (A) in an amount ranging from 0.1 to 250 parts by weight, and preferably 2 to 100 parts by weight per 100 parts by weight of aminofunctional organopolysiloxane component (A)(i).

Water, component (A)(iii) forms the remainder of microemulsion (A) in the optically clear shampoo compositions of this invention. There must be sufficient water present to form a transparent mixture. Generally water is present at a level of from about 10 to 900 parts by weight, preferably from about 80 to about 900 parts by weight per 100 parts by weight of aminofunctional organopolysiloxane (A)(i).

The microemulsions of this invention can be prepared by two different methods. The first is the mechanical method described in U.S. Pat. No. 4,620,878 issued Nov. 6, 1986, which is hereby incorporated by reference herein. The method involves forming a "translucent concentrate" of surfactant, aminofunctional polysiloxane, and water in select proportions. The "concentrate" is then rapidly dispersed in additional water to form the microemulsion. The second method by which the microemulsions of this invention are produced is described in European Patent No. 0459500, which teaches a method of producing oil free microemulsions by emulsion polymerization, the method comprising a mixture of at least one aminofunctional siloxane oligomer, cationic or anionic surfactant, nonionic surfactant, catalyst and water whereby the siloxane oligomer is reacted in the presence of water and the surfactants to form the polysiloxane microemulsions. It is further taught that although the order the ingredients are combined in is not critical, it is essential to have agitation during and following the addition of the ingredients and to have achieved or to heat to the polymerization temperature when all the ingredients have been combined.

The aminofunctional organopolysiloxane microemulsion (A) is present in the optically clear shampoo compositions of this invention in an amount from about 0.5 to 10 weight percent (wt %) and preferably about 2 to 6 wt % based on the total weight of the composition.

For the shampoo compositions to be optically clear the Cationic Equivalence of the microemulsions are preferably less than 0.15. For purposes of this invention, the term "Cationic Equivalence" is used to define the number of equivalents or milliequivalents (depending on the data source) of cationic functionality per gram of sample. It is critical to the compositions of this invention that a microemulsion be present to provide clear shampoo compositions.

Component (B) is at least one anionic detersive surfactant. Component (B) can be any of the well-known anionic detersive surfactants typically used in shampoo formulations. These anionic detersive surfactants function as cleansing agents and foaming agents in the shampoo compositions of this invention.

The anionic detersive surfactants are exemplified by alkali metal sulforicinates, sulfonated glyceryl esters of fatty acids such as sulfonated monoglycerides of coconut oil acids, salts of sulfonated monovalent alcohol esters such as sodium oleylisethianate, amides of amino sulfonic acids such as the sodium salt of oleyl methyl tauride, sulfonated products of fatty acids nitriles such as palmitonitrile sulfonate, sulfonated aromatic hydrocarbons such as sodium alphanaphthalene monosulfonate, condensation products of naphthalene sulfonic acids with formaldehyde, sodium octahydroanthracene sulfonate, alkali metal alkyl sulfates such as sodium lauryl sulfate, ammonium lauryl sulfate or triethanol amine lauryl sulfate, ether sulfates having alkyl groups of 8 or more carbon atoms such as sodium lauryl ether sulfate, ammonium lauryl ether sulfate, sodium alkyl aryl ether sulfates, and ammonium alkyl aryl ether sulfates, alkylarylsulfonates having 1 or more alkyl groups of 8 or more carbon atoms, alkylbenzenesulfonic acid alkali metal salts exemplified by hexylbenzenesulfonic acid sodium salt, octylbenzenesulfonic acid sodium salt, decylbenzenesulfonic acid sodium salt, dodecylbenzenesulfonic acid sodium salt, cetylbenzenesulfonic acid sodium salt, and myristylbenzenesulfonic acid sodium salt, sulfuric esters of polyoxyethylene alkyl ether including $CH_3(CH_2)_6CH_2O(C_2H_4O)_2SO_3H$, $CH_3(CH_2)_7CH_2O(C_2H_4O)_{3.5}SO_3H$, $CH_3(CH_2)_8CH_2O(C_2H_4O)_8SO_3H$, $CH_3(CH_2)_{19}CH_2O(C_2H_4O)_4SO_3H$, and $CH_3(CH_2)_{10}CH_2O(C_2H_4O)_6SO_3H$, sodium salts, potassium salts, and amine salts of alkylnaphthylsulfonic acid.

Preferably Component (B) is selected from the group consisting of sodium lauryl sulfate, ammonium lauryl sulfate, triethanolamine lauryl sulfate, sodium lauryl ether sulfate, and ammonium lauryl ether sulfate.

The anionic detersive surfactant (B) is present in the optically clear shampoo compositions of this invention in an amount from about 5 to 50 wt % and preferably about 5 to 25 wt % based on the total weight of the composition.

Component (C) in the shampoo compositions of this invention is at least one foam boosting agent. The foam boosting agent is preferably selected from the group consisting of fatty acid alkanolamides and amine oxides. The fatty acid alkanolamides are exemplified by isostearic acid diethanolamide, lauric acid diethanolamide, capric acid idiethanolamide, coconut fatty acid diethanolamide, linoleic acid diethanolamide, myristic acid diethanolamide, oleic acid diethanolamide, stearic acid diethanolamide, coconut fatty acid monoethanolamide, oleic acid monoisopropanolamide, and lauric acid monoisopropanolamide.

The amine oxides are exemplified by N-cocodimethylamine oxide, N-lauryl dimethylamine oxide, N-myristyl dimethylamine oxide, N-stearyl dimethylamine oxide, N-cocamidopropyl dimethylamine oxide, N-tallowamidopropyl dimethylamine oxide, bis(2-hydroxyethyl) C12-15 alkoxypropylamine oxide.

Preferably Component (C) is selected from the group consisting of lauric acid diethanolamide, N-lauryl dimethylamine oxide, coconut acid diethanolamide, myristic acid diethanolamide, and oleic acid diethanolamide.

The foam boosting agent (C) is present in the optically clear shampoo compositions of this invention in an amount from about 1 to 15 wt % and preferably about 2 to 10 wt % based on the total weight of the composition.

Component (D) in the compositions of this invention is at least one pH adjusting agent. Preferably the agent adjusts the pH within the range of 4 to 9 and more preferably within the range of 5 to 6 in the shampoo compositions of this invention. Any water soluble acid such as a carboxylic acid or a mineral acid is suitable. For example, suitable acids include mineral acids such as hydrochloric acid, sulfuric acid, and phosphoric acid, monocarboxylic acid such as acetic acid and lactic acid, and polycarboxylic acids such as succinic acid, adipic acid, and citric acid.

The pH adjusting agent (D) is present in the optically clear shampoo compositions of this invention in an amount sufficient to provide a pH in the final shampoo composition of from 4 to 9, more preferably from 5 to 6. Preferably the pH adjusting agent is present in an amount from about 0.01 to 3 wt % and preferably about 0.1 to 0.5 wt % based on the total weight of the composition.

Component (E) in the shampoo compositions of this invention is at least one thickening agent. The thickening agents are preferably in sufficient quantities to provide a convenient viscosity. For example, viscosities within the range of 500 to 25,000 centistokes (cS) or more preferably in the range of 3,000 to 7,000 cS as measured at 25° C. are usually suitable. Suitable thickening agents are exemplified by sodium alginate, gum arabic, polyoxyethylene, guar gum, hydroxypropyl guar gum, cellulose derivatives exemplified by methylcellulose, methylhydroxypropylcellulose, hydroxypropylcellulose, polypropylhydroxyethylcellulose, starch, and starch derivatives exemplified by hydroxyethylamylose and starch amylose, locust bean gum, electrolytes exemplified by sodium chloride and ammonium chloride, and saccharides such as fructose and glucose, and derivatives of saccharides such as PEG-120 methyl glucose diolate. Preferably component (E) is selected from the group consisting of cellulose derivatives, saccharide derivatives, and electrolytes. Component (E) can also be a combination of two or more of the above thickening agents exemplified by a combination of a cellulose derivative and any electrolyte, and a starch derivative and any electrolyte.

The thickening agent (E) is present in the optically clear shampoo compositions of this invention in an amount sufficient to provide a viscosity in the final shampoo composition of from 500 to 25,000 cS. Preferably the thickening agent is present in an amount from about 0.05 to 5 wt % and preferably about 0.05 to 2 wt % based on the total weight of the composition.

Other optional components may be added to the shampoo compositions of this invention such as fragrances, preservatives, and botanicals (plant extracts). The optional ingredients can be present up in an amount of up to 5 parts by weight per 100 parts by weight of optically clear shampoo composition, but preferably are present in amount of from 0.1 to 1 part by weight per 100 parts by weight of optically clear shampoo composition.

The shampoo compositions of this invention may be in the form of a gel, paste, or a freely pourable liquid. The shampoo compositions of this invention can be used on the hair of humans or animals to cleanse and improve the appearance of their coats, respectively. The shampoo compositions of this invention are expected to be used by the usual method of adding the shampoo to the hair, massaging the shampoo into the hair and removing the shampoo from the hair by rinsing with water.

The shampoo compositions may be prepared by simply mixing all ingredients together, and stirring them thoroughly. Heat may be applied to improve the dispersion of the ingredients.

In accordance with this invention, "salting out" is used to describe a phenomena whereby a solubilized or dispersed species becomes insolubilized or non-dispersed upon the addition of ionic strength or "salt". The ionic strength may be due to the addition of electrolyte (e.g. NaCl, $NH_4Cl$, etc.) or poly-electrolyte (e.g. ionic polymers) or both.

The turbidity of the liquid samples in the examples delineated below was tested by light scattering according to Corporate Test Method (CTM) 0851 which is described hereinbelow. Turbidity or haze of liquids caused by the presence of suspended particulate matter is measured by light scattering. Light is passed through a flat bottom cell containing the liquid. As the light beam strikes particles in the liquid, some of the light is scattered at right angles to the incident beam and is received by a photomultiplier tube. The photomultiplier tube converts the light energy into an electrical signal which is measured on a meter. The unit of measure is the Nephelometric Turbidity Unit, NTU, and is based on formazin suspensions as standards. The range of turbidities detectable is 0.04 to 1,000 NTU's. Extremely turbid or highly colored solutions may produce low readings.

The viscosity of the liquids in the examples below were measured in a glass capillary viscometer according to Corporate Test Method(CTM) 0004 described hereinbelow. The kinematic viscosity of liquids is determined by measuring the time required for a fixed volume of samples to pass through a calibrated glass capillary using "gravity-flow". The method is based on ASTM D-445, IP 71 and the results are reported in Stokes.

Polyquaternium-11 is a polyvinylpyrrolidone-polydimethylaminoethylmethacrylate dimethylsulfate quaternary ammonium salt. Cocamide DEA is coconut acid diethanolamide.

Nonoxynol-4 is polyoxyethylene (4) nonyl phenyl ether.

EXAMPLES

Silicone Microemulsions

1. Silicone Microemulsion A is a translucent, cationic microemulsion having an average droplet size of 30 nm diameter. The microemulsion was prepared by emulsion polymerization (the method of European Patent No. 0459500 described hereinabove). The microemulsion contained about 27 weight percent (wt %) aminofunctional organopolysiloxane fluid having the formula $HOMe_2SiO(Me_2SiO)_x(MeRSiO)_ySiMe_2OH$ wherein R denotes the group —$(CH_2)_3NH_2$ and containing 2 mole percent (mol %) y units, about 3 wt % dimethylsiloxane cyclics, 4 wt % tallow trimethyl ammonium chloride, about 8 wt % C11-15 ethoxylated lauryl alcohol, and about 58 wt % water. The silicone microemulsion also contained a preservative (Chloromethyl Isothiazolin-3-One).

2. Silicone Microemulsion B is a translucent, cationic microemulsion having an average droplet size of 30 nm diameter. The microemulsion was prepared by emulsion polymerization (the method of European Patent No. 0459500 described hereinabove). The microemulsion contained about 27 wt % aminofunctional organopolysiloxane fluid having the formula $HOMe_2SiO(Me_2SiO)_x(MeRSiO)_ySiMe_2OH$ wherein R denotes the group —$(CH_2)_3NH(CH_2)_2NH_2$ and containing 2 mol % y units, about 3 wt % dimethylsiloxane cyclics, about 4 wt % tallow trimethyl-ammonium chloride, about 8 wt % ethoxylated lauryl alcohol, and 58 wt % of water. The silicone microemulsion also contained a preservative (Chloromethyl Isothiazolin-3-One).

3. Silicone Microemulsion C is a transparent, nonionic microemulsion having an average droplet size of 30 nm diameter. The microemulsion was prepared by the mechanical method of U.S. Pat. No. 4,620,878 incorporated by reference hereinabove. The microemulsion contained about 14 wt % aminofunctional organopolysiloxane fluid having the formula $Me_3SiO(Me_2SiO)_x(MeRSiO)_ySiMe_3$ wherein R denotes the group —$CH_2CH(CH_3)CH_2NH(CH_2)_2NH_2$, x having a value of about 390 and y having a value of about 8, about 2 wt % dimethylsiloxane cyclics, about 3 wt % polyethoxylated decyl alcohol, about 3 wt % $CH_3(CH_2)_{12}O(EO)_nCH_2COOH$, about 0.3 wt % of triethanolamine, about 7 wt % octylphenoxy polyethoxy (40) ethanol (70 percent in water), and about 71 wt % water.

4. Silicone Microemulsion D is a transparent, nonionic microemulsion having an average droplet size of 30 nm diameter. The microemulsion was prepared by the mechanical method of U.S. Pat. No. 4,620,878 incorporated by reference hereinabove. The composition contains about 15 wt % aminofunctional organopolysiloxane fluid having the formula $Me_3SiO(Me_2SiO)_x(MeRSiO)_ySiMe_3$ wherein R denotes the group —$CH_2CH(CH_3)CH_2NH(CH_2)_2NH_2$, x having a value of about 96 and y having a value of about 2, about 2.5 wt % trimethyl nonyl polyethylene glycol ether, about 3.9 wt % $CH_3(CH_2)_{12}O(EO)_nCH_2COOH$, about 0.3 wt % triethanolamine, about 10 wt % octylphenoxy polyethoxy (40) ethanol (70 percent in water), and about 68 wt % water.

5. Silicone Microemulsion E is a transparent, anionic microemulsion having an average droplet size of 25 nm diameter. The microemulsion was prepared by emulsion polymerization (the method of European Patent No. 0459500 described hereinabove). The microemulsion contained about 18 wt % of a hydroxydimethylsiloxy-terminated polydimethylsiloxane having a viscosity of 20,000 cP, about 2 wt % of unpolymerized dimethylsiloxane cyclics, 7.7 wt % triethanolamine dodecylbenzene sulfonate, and 5.6 wt % of polyoxyethylene (40) octylphenyl ether, and 67 wt % water. The silicone microemulsion also contained a preservative (Chloromethyl Isothiazolin-3-One).

6. Silicone Microemulsion F is a cloudy yellowish cationic microemulsion having an average droplet size of 65 nm diameter. The emulsion was prepared by emulsion polymerization (by the method of European Patent No. 0459500 described hereinabove). The microemulsion contained about 30 wt % hydroxydimethylsiloxy-terminated dimethylsiloxane-methylsilsesquioxane gel, about 1 wt % unpolymerized dimethylsiloxane cyclics, and 4.7 wt % of a secondary alcohol ethoxylate, and 10.3 wt % of Ethoquad T13 27W (an ethoxylated quaternary ammonium salt). The composition contained about 54 wt % water. The silicone microemulsion also contained a preservative (Chloromethyl Isothiazolin-3-One).

7. Silicone Microemulsion G is a clear to slightly yellowish cationic microemulsion having an average droplet size of 30 nm diameter. The emulsion was prepared by the emulsion polymerization of dimethylsiloxane cyclics and contained about 30 wt % hydroxydimethylsiloxy-terminated dimethylsiloxane-aminoethylaminopropylsilsesquioxane having the formula $HOMe_2SiO(Me_2SiO)_x(RSiO_{3/2})_y SiMe_2OH$ wherein R is a group having the formula $—(CH_2)_3 NH(CH_2)_2NH_2$ having 99.4 mol % dimethylsiloxane groups and 0.6 mol % aminoethylaminopropylsilsesquioxane groups, about 5 wt % of unpolymerized dimethylsiloxane cyclics, about 5.8 wt % tallow trimethyl ammonium chloride, about 9.5 wt % of an ethoxylated nonyl alcohol, 48.4 wt % water, and 1 wt % sodium dihydrogen phosphate. The silicone microemulsion also contained a preservative (Chloromethyl Isothiazolin-3-One).

8. Silicone Microemulsion H is a transparent, nonionic microemulsion. The microemulsion was prepared by the mechanical method of U.S. Pat. No. 4,620,878 incorporated by reference hereinabove. The microemulsion contained about 20 wt % of an aminofunctional organopolysiloxane fluid having the formula $Me_3SiO(Me_2SiO)_x(MeRSiO)_y SiMe_3$ wherein R denotes the group $—CH_2CH(CH_3) CH_2NH(CH_2)_2NH_2$, x having a value of about 390 and y having a value of about 8, about 3 wt % of trimethyl nonyl polyethylene glycol ether, about 2 wt % of polyethylene glycol ether of a linear alcohol, about 0.4 wt % acetic acid, and about 74.6 wt % water.

Example I

The following samples were prepared as described hereinbelow:

Sample 1

A shampoo composition was prepared by mixing 670 g of water, 10 g hydroxypropylmethylcellulose, 350 g of 30 wt % ammonium lauryl sulfate, and 30 g of cocamide DEA (coconut acid diethanolamide).

Sample 2

A second shampoo composition was prepared by mixing 670 g of water, 350 g of 30 wt % ammonium lauryl sulfate, and 30 g of cocamide DEA.

Sample 3

A pre-gel composition was prepared by mixing 995 g of water, and 5 g of Carbomer 934 (carboxymethylcellulose).

Sample 4

A conditioner composition was prepared by mixing 985 g of water, and 15 g hydroxyethylcellulose.

Sample 5

A shampoo composition was prepared as in sample 2, except that the pH of that composition was adjusted to 6 with aqueous citric acid, then ammonium chloride was added to the mixture until a viscosity of 7000 centistokes (cS) was reached.

Sample 6

A shampoo composition was prepared by mixing 50 g sodium lauryl ether (2) sulfate, 2 g lauramide DEA (lauric acid diethanolamide), and 48 g water, then adjusting the pH of the mixture to 6 with citric acid, and then adding sodium chloride to the mixture until a viscosity of 7000 cS is reached.

Sample 7

A shampoo composition was prepared by mixing 18 g of the shampoo of sample 2, 1.1 g of Microemulsion H, adjusting the pH of the mixture to 6 with Citric Acid, then adding 0.10 g of 0.5 wt % Ammonium Chloride.

Sample 8

A shampoo composition was prepared by mixing 18 g of the shampoo of sample 2, 1.1 g of Microemulsion E, adjusting the pH of the mixture to 6 with Citric Acid, then adding 0.10 g of 0.5 wt % Ammonium Chloride.

Sample 9

A shampoo composition was prepared by mixing 18 g of the shampoo of sample 2, 0.7 g of Microemulsion H, adjusting the pH of the mixture to 6 with Citric Acid, then adding 0.10 g of Ammonium Chloride.

Sample 10

A shampoo composition was prepared by mixing 18 g of the shampoo of sample 2, 0.7 g of Microemulsion E, adjusting the pH of the mixture to 6 with Citric Acid, then adding 0.10 g of Ammonium Chloride.

Sample 11

A shampoo composition was prepared by mixing 18 g of the shampoo of sample 2, 0.35 g of Microemulsion H, adjusting the pH of the mixture to 6 with Citric Acid, then adding 0.10 g of Ammonium Chloride.

Sample 12

A shampoo composition was prepared by mixing 18 g of the shampoo of sample 2, 0.35 g of Microemulsion E, adjusting the pH of the mixture to 6 with Citric Acid, then adding 0.10 g of Ammonium Chloride.

Sample 13

A shampoo composition was prepared by mixing 15 g of the shampoo of sample 2, 0.9 g of Microemulsion C, adjusting the pH of the mixture to 5 with Citric Acid, then adding 0.10 g of 0.67 wt % Ammonium Chloride.

Sample 14

A shampoo composition was prepared by mixing 15 g of the shampoo of sample 2, 0.9 g of Microemulsion D, adjusting the pH of the mixture to 5 with Citric Acid, then adding 0.10 g of 0.67 wt % Ammonium Chloride.

Sample 15

A shampoo composition was prepared by mixing 60 g of the shampoo of sample 2, 3.6 g of Microemulsion F, adjusting the pH of the mixture to 5.6 with Citric Acid, then adding 0.28 g of Ammonium Chloride.

Sample 16

A shampoo composition was prepared by mixing 60 g of the shampoo of sample 2, 3.6 g of Microemulsion A, adjusting the pH of the mixture to 5.8 with Citric Acid, then adding 0.24 g of Ammonium Chloride.

Sample 17

A shampoo composition was prepared by mixing 60 g of the shampoo of sample 2, 3.6 g of Microemulsion G, adjusting the pH of the mixture to 5.8 with Citric Acid, then adding 0.24 g of Ammonium Chloride.

Sample 18

A shampoo composition was prepared by mixing 30 g of the shampoo of sample 1, 1.8 g of Microemulsion E, adjusting the pH of the mixture to 5 with Citric Acid, then adding 0.21 g of Ammonium Chloride.

Sample 19

A shampoo composition was prepared by mixing 30 g of the shampoo of sample 1, 1.8 g of Microemulsion F, adjusting the pH of the mixture to 5 with Citric Acid, then adding 0.16 g of Ammonium Chloride.

Sample 20

A shampoo composition was prepared by mixing 30 g of the shampoo of sample 1, 1.8 g of Microemulsion A, adjusting the pH of the mixture to 5 with Citric Acid, then adding 0.16 g of Ammonium Chloride.

Sample 21

A shampoo composition was prepared by mixing 30 g of the shampoo of sample 1, 1.8 g of Microemulsion G, adjusting the pH of the mixture to 5 with Citric Acid, then adding 0.16 g of Ammonium Chloride.

Sample 22

A shampoo composition was prepared by mixing 30 g of the shampoo of sample 1, 0.6 g of Microemulsion C, adjusting the pH of the mixture to 5 with Citric Acid, then adding 0.16 g of Ammonium Chloride.

Sample 23

A shampoo composition was prepared by mixing 30 g of the shampoo of sample 1, 1.2 g of Microemulsion C, adjusting the pH of the mixture to 5 with Citric Acid, then adding 0.21 g of Ammonium Chloride.

Sample 24

A shampoo composition was prepared by mixing 30 g of the shampoo of sample 1, 1.8 g of Microemulsion C, adjusting the pH of the mixture to 5 with Citric Acid, then adding 0.16 g of Ammonium Chloride.

Sample 25

A shampoo composition was prepared by mixing 5 g of Microemulsion C with 5 g of 30 wt % of sodium lauryl ether sulfate. A bluish hazy solution was formed. This sample was prepared according to Example 24 of U.S. Pat. No. 4,620,878.

The shampoo compositions described above were then tested utilizing the following procedure. Hair tresses were shampooed with a Shampoo Blank and then dried. Next, 0.5 g of the test shampoo was applied to the hair after it was rewetted. The shampoo was lathered on the hair with rubbing for 30 seconds and then rinsed off in running tap water for 30 seconds. Each tress was detangled by hand combing (once through with a wide part of the comb). The hair tresses were then hung up to dry. The shampoos were then evaluated after 24 hours and tested for clarity (through visual observation), wet combing (wc), wet feel (wf), dry combing (dc), dry feel (df). The results of the above described test are detailed in Table I as shown below.

TABLE I

| Shampoo Composition | SHAMPOO/CONDITIONING | | | | |
|---|---|---|---|---|---|
| | Clarity | Initial wc | wf | dc | df |
| SAMPLE | | | | | |
| 5 | clear | 3.5 | 3 | 3 | 3 |
| 6 | clear | 4 | 2.5 | 3 | 3 |
| 7 | clear | 1.5 | 2 | 2 | 2 |
| 8 | slight haze | 2.5 | 2.5 | 2 | 2 |
| 9 | clear | 2 | 2 | 2 | 2 |
| 10 | slight haze | 3 | 3 | 2 | 2 |
| 11 | clear | 3 | 3 | 2.5 | 3 |
| 12 | slight haze | 3.5 | 3 | 2 | 3 |
| 13 | clear | 1.75 | 2 | 1.5 | 2 |
| 14 | clear | 3 | 2 | 1.5 | 2 |
| 15 | opaque | — | — | — | — |
| 16 | clear-thin | — | — | — | — |
| 17 | opaque | — | — | — | — |
| 18 | slight haze | — | — | — | — |
| 19 | opaque | — | — | — | — |
| 20 | clear | 4 | 2 | 2 | 2 |
| 21 | opaque | — | — | — | — |
| 22 | clear | 4 | 3 | 1.5 | 2 |
| 23 | clear | 2 | 2 | 1.5 | 1.5 |
| 24 | clear | 1.5 | 2 | 2 | 1 |
| 25 | hazy | 4 | 3 | 3 | 3 |

This example illustrates the preference of aminoalkyl functional microemulsions over polydimethylsiloxane microemulsions for shampoo clarity. It also shows the preference for a cationic equivalence of less than 0.15 for the aminofunctional microemulsions. It also illustrates the fact that the aminofunctional microemulsion is preferred to be used at less than 50 wt %, but greater than or equal to 4 wt % in the shampoo for clarity, good aesthetics, and combing. It shows that when the aminofunctional microemulsions are used at a concentration of between 4 and 50 percent with a nonionic or cationic material, aminofunctional microemulsions unexpectedly provide superior shampoo clarity, combing, and aesthetic properties when compared to those in the art.

Example II

This example illustrates the clarity of the compositions of this invention. Samples 15–18 and 22–24 of Example I were tested for their turbidity according to Corporate Test Method (CTM) 0851 described hereinabove. The results of these tests are described in Table II below.

TABLE II

TURBIDITY OF SAMPLES

| SAMPLE | CLARITY | NTU'S |
|---|---|---|
| 15 | opaque | >2,000 |
| 16 | clear-thin | 4.63 |
| 17 | opaque | 53.1 |
| 18 | slight haze | 32.6 |
| 22 | clear | 4.73 |
| 23 | clear | 7.99 |
| 24 | clear | 7.24 |

This example further illustrates that the use of a nonionic or a cationic material in combination with aminofunctional microemulsions having low cationic equivalence produces a turbidity of less than 10 NTU's which provides a clear shampoo. It is further shown that the polydimethylsiloxane microemulsions produce nonclear shampoos.

Comparative Example I

This example further illustrates the aesthetic value and clarity of this invention over the compositions of the art. Samples 23, 24, and 25 were further tested for clarity (through visual observation), wet combing (wc), wet feel (wf), dry combing (dc), dry feel (df), viscosity (according to CTM 0004 described hereinabove) in cS, and aesthetics. The results of these tests are shown in Table III below.

TABLE III

SHAMPOO CHARACTERISTICS

| Sample | clarity | wc | wf | dc | df | viscosity | Aesthetics |
|---|---|---|---|---|---|---|---|
| 25 | very hazy | 4 | 3 | 3 | 3 | 4.79 cS | hair is heavy, combing drag, high static |
| 23 | clear | 2 | 2 | 1.5 | 1.5 | 922.9 cS | hair is light, easy combing, low static |
| 24 | clear | 1.5 | 2 | 2 | 1 | 155.8 cS | Hair is light, easily combed, low static |

The results of Comparative Example I show that the shampoo of Sample 25 was hazy, too thin which resulted in the shampoo running off the hair and hands, and that it was too heavily released onto the hair resulting in heavily coated, limp, and static filled hair after its application and use. In contrast, the application and use of the shampoos of Samples 23 and 24 resulted in an acceptable viscosity formulation such that a light coating was released onto the hair, the formulation clear, and the hair was left well conditioned after its use. Therefore, Samples 23 and 24 represent operative shampoos while Sample 25 does not.

Example III

The following samples were prepared by mixing the ingredients described in Table IV below. The samples were then evaluated to determine the amount of preparation time it took to form a shampoo composition.

TABLE IV

| Composition | SAMPLE 26 | SAMPLE 27 | SAMPLE 28 |
|---|---|---|---|
| water | 118.3 | 118.3 | 125.5 |
| 30 wt % ammonium lauryl sulfate | 66.7 | 66.7 | 66.7 |
| Cocamide DEA | 9.0 | 9.0 | 9.0 |
| Microemulsion E | 9.0 | — | — |
| Microemulsion C | — | 12.0 | — |
| Trimethylsilyl-amodimethicone | — | — | 1.8 |
| Method of Addition | Add-in | Add-in | premix |
| Time required to prepare | 15 min. | 15 min. | 24 hours |
| Citric Acid (30 wt %) Ammonium Chloride | pH 5.7 | pH 5.7 | pH 5.7 |
| A | 0 | 0 | 0 |
| B | 0.15 g | 0.15 g | 0.15 g |
| C | 0.45 g | 0.45 g | 0.45 g |
| D | 0.84 g | 0.78 g | 0.80 g |
| E | 1.10 g | 1.11 g | 1.05 g |
| F | 1.35 g | 1.37 g | 1.37 g |

This example illustrates the ability of the aminofunctional microemulsions to be used by simply mixing the ingredients in contrast to some compositions of the art which require a premixing step which takes 24 hours to produce a shampoo composition.

Example IV

Samples 26–28 of Example III were then prepared by mixing an amount of sample and an amount of ammonium chloride as described in TABLE V below. These formulations were prepared to test each sample's resistance to the salting out phenomenon described hereinabove. The samples were tested for their appearance(visually) after 24 hours, their viscosity (CTM 0004 described hereinabove), and their clarity (haze value) according to CTM 0851 also described hereinabove. The results are displayed in Table V below.

TABLE V

SALTING OUT DETERMINATION

| SAMPLE | NH4Cl | APPEARANCE (24 hrs) | VISCOSITY (cS) (72 hrs) | HAZE (NTU'S) |
|---|---|---|---|---|
| 26A | 0 | slightly hazy | 39.4 | 22.9 |
| 26B | 0.5 | slightly hazy | 920.2 | 25.8 |
| 26C | 1.5 | slightly hazy | 932 | 19.5 |
| 26D | 2.8 | slightly hazy | 65 | 11.01 |
| 26E | 3.667 | separates | 41.5 | 16.1 |
| 26F | 4.5 | separates | 16.7 | 22.3 |
| 27A | 0 | clear | 23.92 | 2.42 |
| 27B | 0.5 | clear | 108.4 | 3.36 |
| 27C | 1.5 | clear | 284 | 5.94 |
| 27D | 2.6 | clear | 128.3 | 11.90 |
| 27E | 3.7 | oiling out | 72.7 | 27.0 |
| 27F | 4.567 | opaque | 62.8 | >2000 |
| 28A | 0 | clear | 11.02 | 2.16 |
| 28B | 0.5 | clear | 29.83 | 3.41 |
| 28C | 1.5 | clear | 477 | 6.09 |
| 28D | 2.667 | clear | 210.9 | 9.85 |
| 28E | 3.5 | clear | 124.4 | 14.6 |
| 28F | 4.567 | oiling out | 91.2 | 30.4 |

This example illustrates the ability of this invention to resist salting out to comparable degrees as compositions existing in the art. It also illustrates the preference for aminofunctional microemulsions over polydimethylsiloxane microemulsions to attain shampoo clarity.

Example V

The following shampoo formulations were prepared by mixing the ingredients described in Table VI below. This example compares the characteristics of a shampoo composition containing aminofunctional microemulsions in contrast to shampoo compositions containing polydimethylsiloxane microemulsions. Samples 29–32 were tested for appearance (through visual observation), wet combing (wc), wet feel (wf), dry combing (dc), dry feel (df), viscosity (according to CTM 0004 described hereinabove) in cS, and clarity (according to Corporate Test Method (CTM) 0851 described hereinabove). The results are shown in Table VI below.

TABLE VI

CHARACTERISTICS OF SHAMPOO COMPOSITION

| Composition | SAMPLE 29 | SAMPLE 30 | SAMPLE 31 |
|---|---|---|---|
| SAMPLE 5 (unneutralized, no salt) | 30 g | 30 g | 30 g |
| Microemulsion E | 1.35 g | — | — |
| Microemulsion C | — | 1.8 g | — |
| Citric Acid | pH 5.8 | pH 5.8 | pH 5.8 |
| Ammonium Chloride | 0.11 | 0.11 | 0.10 |
| RESULTS | | | |
| Appearance | slight haze | clear | clear |
| wet feel | 3 | 3 | 3 |
| wet combing | 3 | 1 | 4 |
| dry combing | 2 | 2 | 3 |
| dry feel | 2 | 2 | 3 |
| viscosity (cs) | 2906 | 412.1 | 10,000 |
| haze (NTU's) | 22.1 | 3.48 | 5 |

This example illustrates that the amino-functional microemulsion shampoo compositions provide better conditioning (wet combing) than do the compositions of the art. They also provide greater clarity. The aminofunctional microemulsions provide the best overall hair care properties when compared to polydimethylsiloxane microemulsions. Also, the amino-functional microemulsions of this invention unexpectedly provided a clearer composition than the blank in the above example.

Example VI

The following formulations were prepared by mixing the ingredients described in Table VII below. These formulations were tested for appearance (through visual observation), wet combing (wc), wet feel (wf), dry combing (dc), dry feel (df), viscosity (through visual observation). The results are shown in Table VII below.

TABLE VII

CHARACTERISTICS OF SHAMPOO COMPOSITION

| Composition | SAMPLE 33 | SAMPLE 34 | SAMPLE 35 |
|---|---|---|---|
| Water | 18.2 | 17.3 | Blank |
| Cocamide DEA | 0 | 0.9 | Sample 5 |
| Ammonium Lauryl - Sulfate (30 wt %) | 10.0 | 10.0 | — |
| Microemulsion C | 1.8 | 1.8 | — |
| Citric Acid (30 wt %) | pH 5.2 | pH 5.2 | |
| Ammonium Chloride | 0.36 | 0.36 | — |
| RESULTS | | | |
| Appearance | clear homogenous | clear homogenous | clear homogenous |
| Wet Feel | 3 | 3 | 3 |
| Wet Combing | 3 | 4 | 4 |
| Dry Combing | 2 | 2 | 3 |
| Dry Feel | 2 | 2 | 3 |
| Viscosity | very thin | medium | good |

This example illustrates that Cocamide DEA can act as a viscosity builder in this invention. This example further illustrates that the use of an aminofunctional microemulsion produces an optically clear shampoo composition with good conditioning properties and cleaning properties in one composition.

What is claimed is:

1. An optically clear shampoo composition comprising:
   (A) an aminofunctional silicone microemulsion having an average particle size of less than 0.14 microns comprising:
      (i) an aminofunctional polyorganosiloxane having its formula selected from the group consisting of $R_3SiO(R_2SiO)_x(RQSiO)_ySiR_3$ and $HOR_2SiO(R_2SiO)_x(RQSiO)_ySiR_2OH$ wherein R is selected from the group consisting of alkyl, aryl, and alkenyl radicals, Q is a polar radical having the formula —R'NHR² wherein R' is a divalent linking group composed of carbon and hydrogen atoms having from 2 to 10 carbon atoms, and $R^2$ is selected from the group consisting of a hydrogen atom, alkyl radicals containing from 1 to 4 carbon atoms, and the —$CH_2CH_2NH_2$ radical, the value of y is at least one, and the sum of x+y is less than 500;
      (ii) a surfactant which is insoluble in the polyorganosiloxane; and
      (iii) water;
   (B) at least one anionic detersive surfactant;
   (C) at least one foam boosting agent;
   (D) at least one pH adjusting agent;
   (E) at least one thickening agent; and
   (F) water.

2. A composition according to claim 1, wherein R is methyl, Q is a polar radical having the formula —R'NHCH₂CH₂NH₂, R' is selected from the group consisting of propylene, and —$CH_2CH(CH_3)CH_2$—.

3. A composition according to claim 1, wherein (A)(ii) is selected from the group consisting of anionic surfactants, cationic surfactants, nonionic surfactants, amphoteric surfactants, combinations of 2 or more types of nonionic surfactants, combinations of nonionic surfactants and anionic surfactants, and combinations of nonionic surfactants and cationic surfactants.

4. A composition according to claim 3, wherein the anionic surfactants are selected from the group consisting of alkali metal sulforicinates, sulfonated glyceryl esters of fatty acids, salts of sulfonated monovalent alcohol esters, amides of amino sulfonic acids, sulfonated products of fatty acids nitrites, sulfonated aromatic hydrocarbons, condensation products of naphthalene sulfonic acids with formaldehyde, sodium octahydroanthracene sulfonate, alkali metal alkyl sulfates, ether sulfates having alkyl groups of 8 or more carbon atoms, alkylarylsulfonates having 1 or more alkyl groups having 8 or more carbon atoms, alkylbenzenesulfonic acid alkali metal salts, sulfuric esters of polyoxyethylene alkyl ether, alkylnaphthylsulfonic acid sodium salts, alkylnaphthylsulfonic acid potassium salts, and alkylnaphthylsulfonic acid amine salts.

5. A composition according to claim 3, wherein the cationic surfactants are selected from the group consisting of fatty acid amines, fatty acid amides, fatty acid amine salts, fatty acid amide salts.

6. A composition according to claim 3, wherein the nonionic surfactants are selected from the group consisting of polyoxyethylene alkyl ethers, polyoxyethylene alkylphenol ethers, polyoxyethylene lauryl ethers, polyoxyethylene sorbitan monoleates, polyoxyethylene alkyl esters, polyoxyethylene sorbitan alkyl esters, polyethylene glycol, polypropylene glycol, diethylene glycol, ethoxylated trimethylnonanols, and polyoxyalkylene glycol modified polysiloxanes.

7. A composition according to claim 3, wherein the amphoteric surfactants are selected from the group consisting of amino acid surfactants and betaine acid surfactants.

8. A composition according to claim 1, wherein (A)(ii) is selected from the group consisting of 2,6,8-trimethyl-4-nonyloxypolyethylene oxyethanol, 2,6,8-trimethyl-4-nonyloxypolyethylene oxyethanol, alkyleneoxypolyethylene oxyethanol, octylphenoxy polyethoxy ethanols, nonionic ethoxylated tridecyl ethers, alkali metal salts of dialkyl sulfosuccinates, polyethoxylated quaternary ammonium salts, ethylene oxide condensation products of primary fatty amines, and polyoxyalkylene glycol modified polysiloxanes.

9. A composition according to claim 1, wherein (B) is selected from the group consisting of selected from the group consisting of alkali metal sulforicinates, sulfonated glyceryl esters of fatty acids, salts of sulfonated monovalent alcohol esters, amides of amino sulfonic acids, sulfonated products of fatty acids nitrites, sulfonated aromatic hydrocarbons, condensation products of naphthalene sulfonic acids with formaldehyde, sodium octahydroanthracene sulfonate, alkali metal alkyl sulfates, ether sulfates having alkyl groups of 8 or more carbon atoms, alkylarylsulfonates having 1 or more alkyl groups having 8 or more carbon atoms, alkylbenzenesulfonic acid alkali metal salts, sulfuric esters of polyoxyethylene alkyl ether, alkylnaphthylsulfonic acid sodium salts, alkylnaphthylsulfonic acid potassium salts, and alkylnaphthylsulfonic acid amine salts.

10. A composition according to claim 1, wherein (B) is selected from the group consisting of sodium lauryl sulfate, ammonium lauryl sulfate, triethanolamine lauryl sulfate, sodium lauryl ether sulfate, and ammonium lauryl ether sulfate.

11. A composition according to claim 1, wherein (C) is selected from the group consisting of fatty acid alkanolamides and amine oxides.

12. A composition according to claim 11, wherein the fatty acid alkanolamides are selected from the group consisting of isostearic acid diethanolamide, lauric acid diethanolamide, capric acid diethanolamide, coconut fatty acid diethanolamide, linoleic acid diethanolamide, myristic acid diethanolamide, oleic acid diethanolamide, stearic acid diethanolamide, coconut fatty acid monoethanolamide, oleic acid monoisopropanolamide, and lauric acid monoisopropanolamide.

13. A composition according to claim 11, wherein the amine oxides are selected from the group consisting of N-cocodimethylamine oxide, N-lauryl dimethylamine oxide, N-myristyl dimethylamine oxide, N-stearyl dimethylamine oxide, N-cocamidopropyl dimethylamine oxide, N-tallowamidopropyl dimethylamine oxide, bis(2-hydroxyethyl) C12-15 alkoxypropylamine oxide.

14. A composition according to claim 1, wherein (C) is selected from the group consisting of lauric acid diethanolamide, N-lauryl dimethylamine oxide, coconut acid diethanolamide, myristic acid diethanolamide, and oleic acid diethanolamide.

15. A composition according to claim 1, wherein (D) is a water soluble acid.

16. A composition according to claim 15, wherein the water soluble acid is selected from the group consisting of carboxylic acids and mineral acids.

17. A composition according to claim 16, wherein the mineral acid is selected from the group consisting of hydrochloric acid, sulfuric acid, and phosphoric acid and the carboxylic acid is selected from the group consisting of acetic acid, lactic acid, succinic acid, adipic acid, and citric acid.

18. A composition according to claim 1, wherein (E) is selected from the group consisting of sodium alginate, gum arabic, polyoxyethylene, guar gum, hydroxypropyl guar gum, cellulose derivatives, starch, starch derivatives, locust bean gum, electrolytes, saccharides, saccharides derivatives, a combination of a cellulose derivative and an electrolyte, and a combination of a starch derivative and an electrolyte.

19. A composition according to claim 1, wherein (E) is selected from the group consisting of cellulose derivatives, saccharide derivatives, and electrolytes.

20. A composition according to claim 18, wherein the cellulose derivative is selected from the group consisting of methylcellulose, methylhydroxypropylcellulose, hydroxypropylcellulose, and polypropylhydroxyethylcellulose, the starch derivative is selected from the group consisting of hydroxyethylamylose and starch amylose, the electrolyte is selected from the group consisting of sodium chloride and ammonium chloride, the saccharide is selected from the group consisting of fructose and glucose, and the saccharide derivative is PEG-20 methyl glucose diolate.

21. A composition according to claim 19, wherein the cellulose derivative is selected from the group consisting of methylcellulose, methylhydroxypropylcellulose, hydroxypropylcellulose, and polypropylhydroxyethylcellulose, the saccharide derivative is PEG-20 methyl glucose diolate, and the electrolyte is selected from the group consisting of sodium chloride and ammonium chloride.

22. A method of shampooing hair comprising:
(I) wetting hair;
(II) applying to the hair an optically clear shampoo composition comprising:
(A) an aminofunctional silicone microemulsion having an average particle size of less than 0.14 microns comprising:
(i) an aminofunctional polyorganosiloxane having its formula selected from the group consisting of

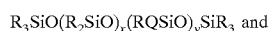

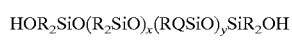

wherein R is selected from the group consisting of alkyl, aryl, and alkenyl radicals, Q is a polar radical having the formula —R'NHR$^2$ wherein R' is a divalent linking group composed of carbon and hydrogen atoms having from 2 to 10 carbon atoms, and $R^2$ is selected from the group consisting of a hydrogen atom, all radicals containing from 1 to 4 carbon atoms, and the —$CH_2CH_2NH_2$ radical, the value of y is at least one, and the sum of x+y is less than 500;
    (ii) a surfactant which is insoluble in the polyorganosiloxane; and
    (iii) water;
(B) at least one anionic detersive surfactant;
(C) at least one foam boosting agent;
(D) at least one pH adjusting agent;
(E) at least one thickening agent; and
(F) water;
(III) massaging the optically clear hair conditioning composition into the hair; and
(IV) rinsing the optically clear hair conditioning composition from the hair with water.

\* \* \* \* \*